(12) United States Patent
Landau et al.

(10) Patent No.: US 10,717,766 B2
(45) Date of Patent: Jul. 21, 2020

(54) ANTIMICROBIAL PEPTIDES AND USES THEREOF

(71) Applicant: TECHNION RESEARCH & DEVELOPMENT FOUNDATION LIMITED, Haifa (IL)

(72) Inventors: Meytal Landau, Haifa (IL); Asher Moshe, Netanya (IL); Nir Salinas, Rishon le Ziyon (IL)

(73) Assignee: TECHNION RESEARCH & DEVELOPMENT FOUNDATION LIMITED, Haifa (IL)

(*) Notice: Subject to any disclaimer, the term of this patent is extended or adjusted under 35 U.S.C. 154(b) by 0 days.

(21) Appl. No.: 16/327,047

(22) PCT Filed: Aug. 22, 2017

(86) PCT No.: PCT/IL2017/050936
§ 371 (c)(1),
(2) Date: Feb. 21, 2019

(87) PCT Pub. No.: WO2018/037408
PCT Pub. Date: Mar. 1, 2018

(65) Prior Publication Data
US 2019/0241624 A1 Aug. 8, 2019

Related U.S. Application Data

(60) Provisional application No. 62/377,716, filed on Aug. 22, 2016.

(51) Int. Cl.
| | | |
|---|---|---|
| *A61K 38/00* | (2006.01) | |
| *A61K 38/10* | (2006.01) | |
| *A61K 38/08* | (2019.01) | |
| *C07K 7/06* | (2006.01) | |
| *C07K 7/08* | (2006.01) | |
| *C07K 14/10* | (2006.01) | |
| *C07K 14/31* | (2006.01) | |
| *A01N 37/18* | (2006.01) | |

(52) U.S. Cl.
CPC .............. *C07K 14/31* (2013.01); *A01N 37/18* (2013.01); *A61K 38/00* (2013.01); *Y02A 50/473* (2018.01); *Y02A 50/481* (2018.01)

(58) Field of Classification Search
CPC ........ A61K 38/00; A61K 38/10; A61K 38/08; C07K 11/10; C07K 7/06; C07K 7/08; C07K 14/31
USPC ... 514/1.1, 2.3, 2.4, 2.6, 2.7, 2.9, 21.8, 21.7, 514/21.6, 21.5, 21.4; 530/300, 329, 328, 530/327, 326
See application file for complete search history.

(56) References Cited

U.S. PATENT DOCUMENTS 8,211,445 B2 * 7/2012 Otto ................. G01N 33/56938
424/185.1
2010/0119477 A1 5/2010 Otto et al.

FOREIGN PATENT DOCUMENTS

WO 2014205111 A1 12/2014

OTHER PUBLICATIONS

T1Y671 from UniProt, pp. 1-4. Integrated into UniProtKB/TrEMBL on Nov. 13, 2013. (Year: 2013).*
Otto, Michael, "Phenol-soluble modulins", Int J Med Microbiol., Mar. 2014, 304(2): 164-169, equivalent pp. 1-15 enclosed. (Year: 2014).*
Gonzalez, et al., "Novel Phenol-soluble Modulin Derivatives in Community-associated Methicillin-resistant *Staphylococcus aureus* Identified through Imaging Mass Spectrometry" Journal of Biological Chemistry, vol. 287 No. 17, pp. 13889-13898. Feb. 27, 2012.
Cheung, et al., "Insight into structure-function relationship in phenol-soluble modulins using an alanine screen of the phenol-soluble modulin (PSM) alpha3 peptide", The FASEB Journal, vol. 28 No. 1, pp. 153-161. Jan. 31, 2014.
Kretschmer, et al. "Peptide length and folding state govern the capacity of *staphylococcal* beta-type phenol-soluble modulins to activate human formyl-peptide receptors 1 or 2", Journal of Leukocyte Biology, vol. 97 No. 4, pp. 689-697. Feb. 27, 2015.
Bahar, et al., "Antimicrobial peptides", Pharmaceuticals, 6(12), pp. 1543-1575. Nov. 28, 2013.
Schwartz, et al., "Microbial Amyloids—Functions and Interactions within the Host", Current Opinion in Microbiology vol. 16, pp. 93-99 (2013).
Kagan, et al., "Antimicrobial Properties of Amyloid Peptides", Molecular Pharmaceutics vol. 9, pp. 708-717 (2012).
Landreh, et al., "Separate Molecular Determinants in Amyloidogenic and Antimicrobial Peptides", Journal of Molecular Biology vol. 426, pp. 2159-2166 (2014).
Kumar, et al., "Amyloid-Beta Peptide protects against Microbial Infection in Mouse and Worm Models of Alzheimer's Disease", Science Translational Medicine vol. 8, No. 340 (2016).
Nelson, et al., "Structure of the Cross-Beta Spine of Amyloid-Like Fibrils", Nature Publishing Group, vol. 435, pp. 773-778 (2005).
Van Melckebeke, et al., "Atomic-Resolution Three-Dimensional Structure of Het-s(218-289) Amyloid Fibrils by Solid-State NMR Spectroscopy" Journal of American Chemical Society vol. 132, pp. 13765-13775 (2010).
Berthelot, et al., "In Vivo and in Vitro Analyses of Toxic Mutants of Het-s: FTIR Antiparallel Signature Correlates with Amyloid Toxicity", Journal of Molecular Biology vol. 412, pp. 137-152 (2011).
Chen, et al., "Structural Characterization of Toxic Oligomers that are Kinetically Trapped during Alpha-Synuclein Fibril Formation", Proceedings of the National Academy of Sciences of the U.S.A. vol. 112, (2015).
Liu, et al., "Out-of-Register Beta-Sheets suggest a pathway to toxic amyloid Aggregates", Proceedings of the National Academy of Sciences of the U.S.A. vol. 109, No. 51, pp. 20913-20918 (2012).
Koczulla, et al., "Antimicrobial Peptides: Current Status and Therapeutic Potential", Drugs vol. 63, pp. 389-406 (2003).

(Continued)

*Primary Examiner* — Julie Ha
(74) *Attorney, Agent, or Firm* — The Roy Gross Law Firm, LLC; Roy Gross

(57) ABSTRACT

A fragment of a virulent peptide named phenol-soluble modulin (PSM) having anti-bacterial activity and methods for eliminating bacteria are provided.

19 Claims, 4 Drawing Sheets

Specification includes a Sequence Listing.

(56) References Cited

OTHER PUBLICATIONS

Kuroda, et al., "The human cathelicidin antimicrobial peptide LI-37 and mimics are potential anticancer drugs", Frontiers in Oncology vol. 5, Article 144 (2015).

Soscia, et al., The Alzheimer's Disease-Associated Amyloid Beta-Protein is an Antimicrobial Peptide. PloS one vol. 3, No. 5, e9505 (2010).

International Search Report and Written Opinion of the Searching Authority for International Application No. PCT/IL2017/050936, dated Oct. 15, 2017.

Joo, et al: "Antimicrobial Activity of Community-associated Methicillin-resistant *Staphylococcus aureus* Is Caused by Phenol-soluble Modulin Derivatives", The Journal of Biological Chemistry, vol. 286, No. 11, pp. 8933-8940, Mar. 18, 2011.

Cheung, et al: "Insight into structure-function relationship in phenol-soluble modulins using an alanine screen of the phenol-soluble modulin (PSM) α3 peptide", The FASEB Journal, vol. 28, No. 1, pp. 153-161, Jan. 1, 2014.

Salinas, N. "Extreme amyloid polymorphism in *Staphylococcus aureus* virulent PSMα peptides", Nature Communications, vol. 9, No. 1, pp. 1-9, Aug. 28, 2018.

Tayeb-Fligelman, et al: "The cytotoxic *Staphylococcus aureus* PSMa3 reveals a cross-a amyloid-like fibril", Science, vol. 355, pp. 831-833, Feb. 24, 2017.

\* cited by examiner

FIGURE 1A
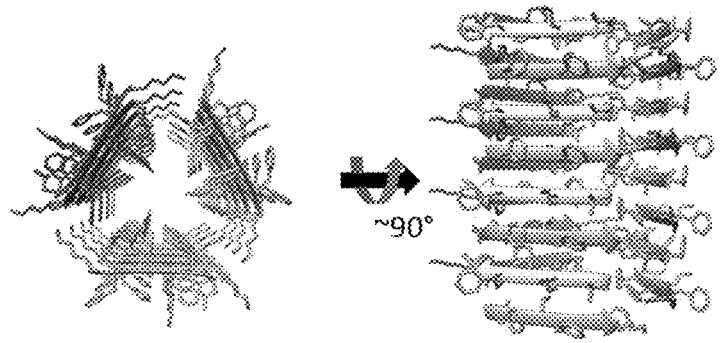
FIGURE 1B
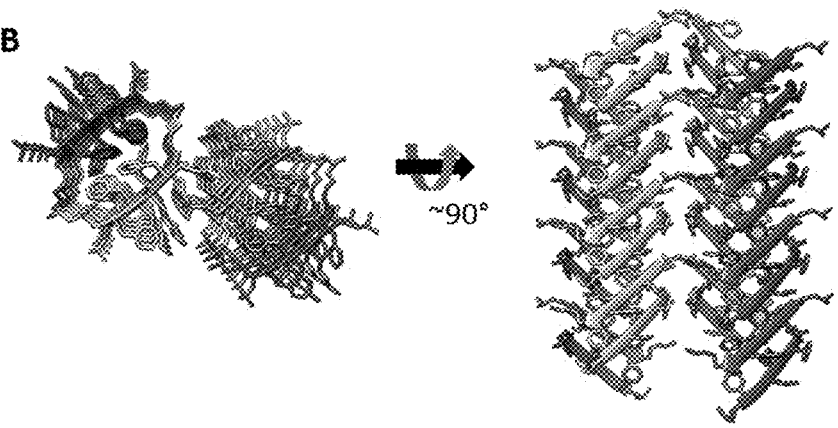
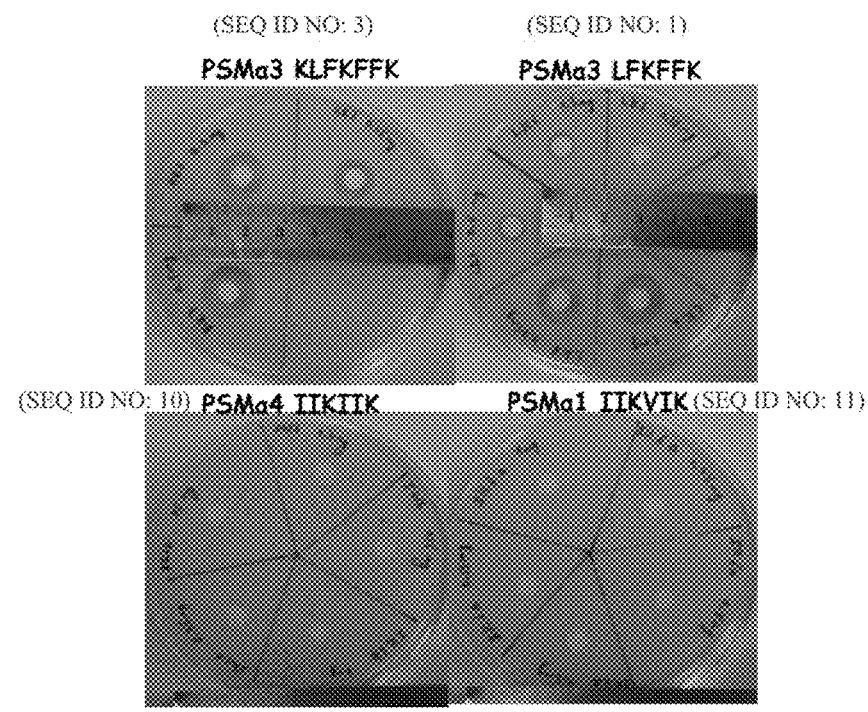
FIGURE 2A

|  | Control (water) | 0.25 mg | 0.5 mg | 1 mg |
|---|---|---|---|---|
| Ac-LFKFFK-NH$_2$ (SEQ ID NO: 1) | | | | |
| Ac-KLFKFFK-NH$_2$ (SEQ ID NO: 3) | | | | |

ANTIMICROBIAL PEPTIDES AND USES THEREOF

CROSS-REFERENCE TO RELATED APPLICATIONS

This application is a National Phase of PCT Patent Application No. PCT/IL2017/050936 having International filing date of Aug. 22, 2017, which claims the benefit of priority of U.S. Provisional Patent Application No. 62/377,716 filed Aug. 22, 2016, the contents of which the above applications are all incorporated by reference as if fully set forth herein in their entirety.

FIELD OF INVENTION

This invention is directed to, inter alia, antimicrobial peptides (AMPs) and their utilization as anti-bacterial agents.

BACKGROUND OF THE INVENTION

Antimicrobial peptides (AMPs) are oligopeptides with a varying number of amino acids (from five to over a hundred). AMPs have a broad spectrum of targeted organisms ranging from viruses to parasites.

The discovery of AMPs dates back to 1939 when Dubos extracted an antimicrobial agent from a soil *Bacillus* strain. This extract was demonstrated to protect mice from pneumococci infection. In the following year, Hotchkiss and Dubos fractionated this extract and identified an AMP which was named gramicidin. Despite some reported toxicity associated with intraperitoneal application, gramicidin was found to be beneficial for topical treatment of wounds and ulcers. In 1941, another AMP, tyrocidine, was discovered and found to be effective against both gram-negative and gram-positive bacteria. However, tyrocidine was toxic to human blood cells. In the same year, another AMP was isolated from a plant *Triticum aestivum*, which was later named purothionin and found to be beneficial against fungi and some pathogenic bacteria.

The first reported animal-originated AMP is defensin, which was isolated from rabbit leukocytes in 1956. In the following years, bombinin from epithelia and lactoferrin from cow milk were both described. During the same time, it was also proven that human leukocytes contain AMPs in their lysosomes.

Most AMPs are produced by specific cells while the production of some AMPs is inducible. Several types of eukaryotic cells are involved in AMP production such as lymph, epithelial cells in gastrointestinal and genitourinary systems, phagocytes, and lymphocytes of the immune system. In addition to direct involvement in innate immunity, AMPs have also been found to influence the host's inflammatory responses during an infection. It is known that lipopolysaccharide (LPS) molecules released from bacteria as a result of antibiotic treatment or host immunity, can induce AMP production in mammals.

Most AMPs are characterized as one of the following four types based on their secondary structures: β-sheet, α-helix, extended, and loop. Among these structural groups, α-helix and β-sheet structures are more common. β-sheet peptides are composed of at least two β-strands with disulfide bonds between these strands.

The best-known examples of such AMPs are protegrin, magainin, cyclic indolicin, and coiled indolicin. Some AMPs contain two different structural components. In addition, many peptides form their active structure only when they interact with the membranes of target cells. For example, indolicin shows globular and amphipathic conformation in aqueous solutions while it is wedge-shaped in lipid bilayer mimicking environments. This AMP also changes its conformation during interaction with DNA.

Understanding the impact of the molecular level of AMPs on their mechanism(s) of action is needed in order to develop a new class of antibiotics. Recently, a correlation between antimicrobial activity and amyloid formation was described.

Fibrils and oligomers amyloids are involved in more than 20 fatal diseases and astonishingly, also in controlled cellular processes in all kingdoms of life. Interestingly, peptides of several well-known human host defense form amyloid-like fibrils, and several well-known human disease-related amyloids, including AP involved in Alzheimer's, display antimicrobial action.

SUMMARY OF THE INVENTION

According to some embodiments of the present invention, there is provided a fragment of a bacterial secreted phenol-soluble modulin (PSM) having an antibacterial activity. In one embodiment, provided herein is a fragment of a *Staphylococcus aureus* secreted phenol-soluble modulin (PSM) having an antibacterial activity.

In some embodiments, the peptide of the invention is a fragment of SEQ ID NO: 2 (MEFVAKLFKFFKDLLGK-FLGNN), or an analog thereof. In some embodiments, the fragment of SEQ ID NO: 2 or analog thereof, comprises SEQ ID NO: 1 (LFKFFK).

In some embodiments, the present invention provides a peptide of up to 20 amino acid residues, the peptide comprising the amino acid sequence as set forth in SEQ ID NO: 1 (LFKFFK).

In some embodiments, the peptide comprises or consists of the acid sequence selected from the group consisting of: SEQ ID NO: 1 (LFKFFK), SEQ ID NO: 3 (KLFKFFK), SEQ ID NO: 4 (KLFKFFKD), SEQ ID NO: 5 (KLFKFFKDL), SEQ ID NO: 6 (KLFKFFKDLL), SEQ ID NO: 7 (KLFKFFKDLLG), SEQ ID NO: 8 (AK-LFKFFKDLLGK), and SEQ ID NO: 9 (VAKLFKFFKDLL-GKFL).

In some embodiments, the N-terminus of the peptide is acetylated.

In some embodiments, the peptide of this invention is characterized by antimicrobial activity. In some embodiments, the peptide of this invention is characterized by antibacterial activity. In one embodiment, the bacteria are Gram-positive bacteria. In one embodiment, the bacteria are Gram-negative bacteria.

In some embodiments, the bacterium is selected from, but not limited to: *Micrococcus luteus, Staphylococcus aureus, Staphylococcus epidermidis, Staphylococcus hominis, Streptococcus agalactiae, Lactobacillus casei, Klebsiella pneumoniae, Enterococcus faecalis, Escherichia coli, Pseudomonas aeruginosa, Salmonella enterica*, or any combination thereof.

In some embodiments, the peptide of this invention is characterized by a minimal inhibition concentration (MIC) of less than 500 μM.

In one embodiment, there is provided a composition comprising the peptide of the present invention and a carrier. In one embodiment, the composition is a pharmaceutical composition. In some embodiments, the pharmaceutical composition comprises a therapeutic effective amount of the peptide with optionally other therapeutic ingredient(s) and one or more pharmaceutically acceptable carriers. In some embodiments, the composition comprises at least three peptides of the invention, wherein said peptides are in the form of antiparallel β-strand.

In another aspect, the present disclosure provides a method for eliminating bacteria or inhibiting growth thereof, the method comprising contacting the bacteria with the peptide or the composition of this invention, thereby eliminating bacteria or inhibiting growth thereof.

In some embodiments, the present invention provides a method for reducing or eliminating bacteria or inhibiting growth thereof, on a surface, comprising contacting the surface with the peptide or the composition of the invention.

In some embodiments, the method for treating a subject afflicted with a bacterial infection, the method comprising administering to the subject an effective amount of the peptide or of the composition of this invention, thereby treating a subject afflicted with a bacterial infection.

In one embodiment, the peptide is in an amount sufficient to eliminate bacteria refractory to a eukaryotic cell. In one embodiment, the peptide is in an amount sufficient to eliminate bacteria but refractory to a eukaryotic cell.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description together with the drawings makes apparent to those skilled in the art how embodiments of the invention may be practiced.

In the drawings:

FIGS. 1A-B illustrate the crystal structures of two forms of LFKFFK (SEQ ID NO: 1). In the left panel, the view looks down the fibril axis, and in the right panel, the view is perpendicular to the fibril axis.

FIG. 2A illustrates the growth of *Micrococcus luteus* after treatment with the peptide of the invention LFKFFK (SEQ ID NO: 1) in the upper left image, and KLFKFFK (SEQ ID NO: 3) in the upper right image, and control peptides with a hydrophobic/cationic amino-acid composition, IIKIIK (SEQ ID NO: 10) (bottom left image) and IIKVIK (SEQ ID NO: 11) (bottom right image), calculated in FIG. 2B.

DETAILED DESCRIPTION OF THE INVENTION

Figures 2B, 3:
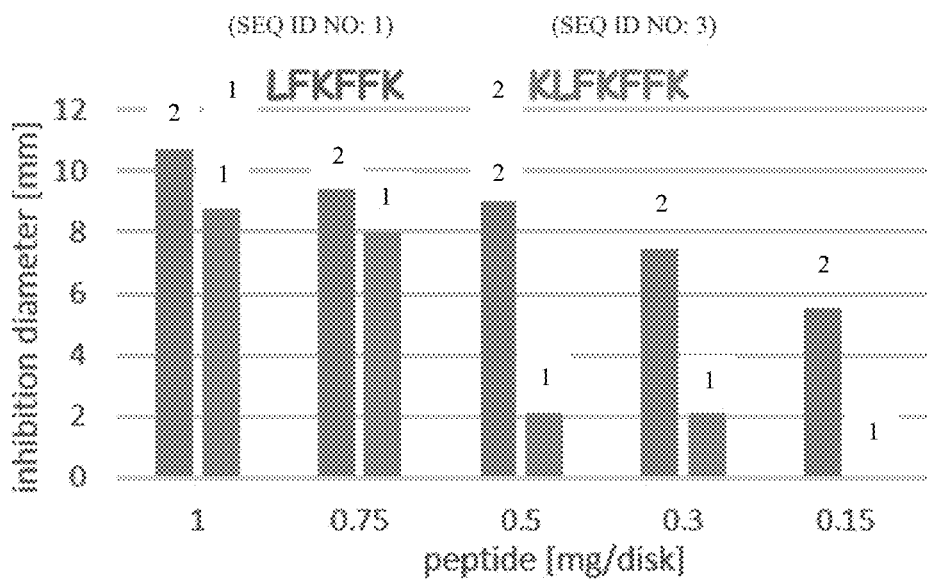
FIG. 2B presents bar graphs demonstrating the diameter of the growth inhibition of *Micrococcus luteus* after treatment with various concentrations of LFKFFK (SEQ ID NO: 1; right bar graph) and KLFKFFK (SEQ ID NO: 3; left bar graph), as illustrated in FIG. 2A.
FIG. 3 illustrates the growth of *Staphylococcus hominis* after treatment with various concentrations of the acetylated peptides: LFKFFK (SEQ ID NO: 1) and KLFKFFK (SEQ ID NO: 3).

In one embodiment, provided herein is a fragment of a bacterial secreted phenol-soluble modulin (PSM) having an antibacterial activity. In one embodiment, provided herein is a fragment of a *Staphylococcus aureus* secreted phenol-soluble modulin (PSM) having an antibacterial activity.

In some embodiments, the peptide of the invention is a fragment of SEQ ID NO: 2 (MEFVAKLFKFFKDLLGK-FLGNN), or an analog thereof. As exemplified herein below, various fragments of SEQ ID NO: 2, comprising the LFKFFK motif, were highly effective in inhibiting growth of various bacteria.

As exemplified herein below, the present invention provides antibacterial peptides that form ordered amyloid fibrils. Surprisingly, the antibacterial peptides were selective against pathogenic bacteria and not probiotic bacteria. As demonstrated herein below, the atomic structure of the antibacterial LFKFFK (SEQ ID NO: 1) peptide shows the formation of elongated beta-sheets running along the fibril axis, with a distance of 4.6-4.8 Angstrom between individual beta-strands. In some embodiments, each peptide forms one beta-strand that self-assemble into the elongated fibril. Notably, LFKFFK (SEQ ID NO: 1) is a derivative of a native full-length peptide, PSMalpha3, secreted by *S. aureus*. PSMalpha3 (SEQ ID NO: 2) lacks antibacterial activity and forms fibrils made out of alpha-helices, and not beta-strands. Without limiting the invention to any theory or mechanism of action, the findings presented herein indicates that the conformational switch (from alpha-helices to beta-strands) accounts for the antibacterial activity.

In some embodiments, the present invention provides a peptide of up to 20 amino acid residues, up to 19 amino acid residues, up to 18 amino acid residues, up to 17 amino acid residues, up to 16 amino acid residues, up to 15 amino acid residues, up to 14 amino acid residues, up to 13 amino acid residues, up to 12 amino acid residues up to 11 amino acid residues, the peptide comprising the amino acid sequence as set forth in SEQ ID NO: 1 (LFKFFK).

In some embodiments, the present invention provides a 6 to 20-mer peptide comprising SEQ ID NO: 1. In some embodiments, the present invention provides a 6 to 18-mer peptide comprising SEQ ID NO: 1. In some embodiments, the present invention provides a 6 to 16-mer peptide comprising SEQ ID NO: 1. In some embodiments, the present invention provides a 6 to 11-mer peptide comprising SEQ ID NO: 1. In some embodiments, the present invention provides a 6 to 10-mer peptide comprising SEQ ID NO: 1. In some embodiments, the present invention provides a 6 to 9-mer peptide comprising SEQ ID NO: 1. In some embodiments, the present invention provides a 6 to 8-mer peptide comprising SEQ ID NO: 1. In some embodiments, the present invention provides a 6 to 7-mer peptide comprising SEQ ID NO: 1. In some embodiments, the present invention provides a 6-mer peptide comprising SEQ ID NO: 1.

In some embodiments, the amino acid sequence of the peptide is selected from the group consisting of: SEQ ID NO: 1 (LFKFFK), SEQ ID NO: 3 (KLFKFFK), SEQ ID NO: 4 (KLFKFFKD), SEQ ID NO: 5 (KLFKFFKDL), SEQ ID NO: 6 (KLFKFFKDLL), SEQ ID NO: 7 (KLFKFFKDLLG), SEQ ID NO: 8 (AKLFKFFKDLLGK), and SEQ ID NO: 9 (VAKLFKFFKDLLGKFL).

In some embodiments, the peptide comprises at least one post-translational modification. In some embodiments, the peptide comprises at least one post-translational modification at the N- or C-termini of said peptide. In some embodiments, the peptide comprises at least one post-translational modification (including but not limited to acetylation and amidation) as long as the modification enhances or does not hamper fibril formation of said peptide. In some embodiments, the peptide is acetylated. In some embodiments, the N-terminus of the peptide is acetylated. As exemplified herein below, N-terminal acetylation of the peptide of the invention improves the peptide antimicrobial potency and enhances fibril formation.

In one embodiment, the peptide comprises or consists of the amino acid sequence acetyl-LFKFFK (SEQ ID NO: 1). In one embodiment, the peptide comprises or consists of the amino acid sequence: acetyl-KLFKFFK (SEQ ID NO: 3). In one embodiment, the peptide comprises or consists of the amino acid sequence: acetyl-KLFKFFKDLL (SEQ ID NO: 6). In another embodiment, the peptide comprises or consists of the amino acid sequence: acetyl-KLFKFFKDLLG (SEQ ID NO: 7). In one embodiment, the peptide comprises or consists of the amino acid sequence: acetyl-AKLFKFFKDLLGK (SEQ ID NO: 8). In another embodiment, the peptide comprises or consists of the amino acid sequence: acetyl-VAKLFKFFKDLLGKFL (SEQ ID NO: 9).

In one embodiment, the peptide is in the form of a β-strand. In one embodiment, a plurality of peptides of the invention form a fibril. In some embodiments, the composition of the invention comprises at least three peptides, wherein said peptides are in the form of antiparallel β-strand.

In one embodiment, a plurality of peptides of the invention form an amyloid fibril having a cylindrical structure. In one embodiment, a plurality of peptides of the invention form an amyloid fibril comprising antiparallel β-sheets. In one embodiment, a plurality of peptides of the invention form a fibril comprising a trimeric configuration of antiparallel β-sheets. In another embodiment, the fibril comprises a plurality of peptides of the present invention.

In some embodiments, the peptide of the invention forms elongated fibrils with a distance of 4.4-5 Angstrom between individual β-strands. In some embodiments, the peptide of the invention forms elongated fibrils with a distance of 4.6-4.8 Angstrom between individual β-strands.

The present invention also contemplates analogs of the peptides disclosed herein, as long as the analogs have antimicrobial activity. The term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

Conservative substitution of amino acids as known to those skilled in the art are within the scope of the present invention. Conservative amino acid substitutions include replacement of one amino acid with another having the same type of functional group or side chain e.g. aliphatic, aromatic, positively charged, negatively charged. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, Proteins, 1984).

The term "conservative substitution" also includes the use of a chemically derivatized residue in place of a non-derivatized residue provided that such peptide displays the requisite function of modulating the antibacterial response as specified herein.

In one embodiment, the present invention provides an antimicrobial peptide (AMP). In another embodiment, the present invention provides an anti-bacterial peptide.

In one embodiment, bacteria for which the peptides provided herein are effective, are gram-positive bacteria. In another embodiment, bacteria for which the peptides provided herein are effective, bacteria are gram-negative bacteria. The bacteria for which the peptides provided herein are effective, are selected from, but not limited to: *Micrococcus luteus, Staphylococcus aureus, Staphylococcus epidermidis, Staphylococcus hominis, Streptococcus agalactiae, Lactobacillus casei, Klebsiella pneumoniae, Enterococcus faecalis, Escherichia coli, Pseudomonas aeruginosa, Salmonella enterica*, or any combination thereof.

In some embodiments, the peptide is characterized by a minimal inhibition concentration (MIC) of less than 50 nM, less than 500 nM, less than 5 less than 25 less than 50 less than 100 μM, less than 500 μM, less than 1 mM, or less than 5 mM, including any value therebetween. Each possibility represents a separate embodiment of the invention.

According to some embodiments of the present invention, the disclosed peptides are for use in inhibiting growth and/or elimination of bacteria.

As used herein, the term "inhibiting", or any grammatical derivative thereof, indicates that at least 20%, 30%, 40%, 50%, 60%, 70%, 80%, 90%, or more, reduction of growth or even elimination of growth in a given time as compared to the growth in that given time of bacteria not being exposed to the treatment as described herein. Each possibility represents a separate embodiment of the invention.

As used herein, the term "elimination", or any grammatical derivative thereof, refers to 100% arrest of growth in a given time as compared to the growth in that given time of bacteria not being exposed to the treatment as described herein.

In one embodiment, peptides of the present invention are non-toxic to eukaryotic cells. In one embodiment, peptides of the present invention are non-toxic to mammalian cells. In one embodiment, an effective dose of the peptide of the present invention is non-toxic to eukaryotic cells. In one embodiment, an effective dose of the peptide of the present invention is non-toxic to mammalian cells.

In some embodiments, there is provided a composition comprising one or more peptides disclosed herein.

Pharmaceutical Compositions

The present invention also contemplates pharmaceutical compositions for human medical use, which comprise at least one peptide of this invention.

In one embodiment, the present invention provides a composition, comprising the peptide of the present invention and a carrier. In some embodiments, the pharmaceutical composition comprises a therapeutic effective amount of the peptide with optionally other therapeutic ingredient(s) and one or more pharmaceutically acceptable carriers.

In one embodiment, the peptide is in an amount sufficient to eliminate bacteria refractory to a eukaryotic cell. In one embodiment, the peptide is in an amount sufficient to eliminate bacteria but refractory to a eukaryotic cell.

In another embodiment, the present invention provides a composition, comprising the peptide of the invention and a buffer.

The pharmaceutical compositions of the invention can be formulated in the form of a pharmaceutically acceptable salt of the peptide of the invention or their analogs thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like. In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

The term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans.

The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfate; and agents for the adjustment of tonicity such as sodium chloride or dextrose are also envisioned. The carrier may constitute, in total, from about 0.1% to about 99.99999% by weight of the pharmaceutical compositions presented herein.

An embodiment of the invention relates to a peptide presented in unit dosage form and is prepared by any of the methods well known in the art of pharmacy. In an embodiment of the invention, the unit dosage form is in the form of a tablet, capsule, lozenge, wafer, patch, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

The compositions may comprise preservatives, such as benzalkonium chloride and thimerosal and the like; chelating agents, such as EDTA sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions may also comprise local anesthetics or other actives.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, compositions of the present invention are presented in a pack or dispenser device, such as an FDA approved kit, which contains one or more unit dosage forms containing the active ingredient. In one embodiment, the pack or dispenser device is accompanied by instructions for administration.

In some embodiments, the composition is in the form of, but not limited to, a liquid, gel, solid or biofumigant. In some embodiments, the composition comprises a surfactant to be used for the purpose of emulsification, dispersion, wetting, spreading, integration, disintegration control, stabilization of active ingredients, and improvement of fluidity or rust inhibition.

Suitable routes of administration include, but are not limited to, oral, parenteral (e.g., intravenous, subcutaneous, intramuscular), intranasal, buccal, topical, rectal, aerosol, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections. In certain embodiments, the composition as described herein is administered in a systemic manner. In certain other embodiments, the composition as described herein is administered in a local rather than a systemic manner.

In another embodiment, the compounds described herein are formulated into pharmaceutical compositions. Pharmaceutical compositions of the invention are formulated in a conventional manner using one or more pharmaceutically acceptable inactive ingredients that facilitate processing of the active compounds into preparations that are used pharmaceutically. A formulation depends upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In another embodiment, a pharmaceutical composition comprises a mixture of a compound of the invention and at least one additional active ingredient. In another embodiment, a pharmaceutical composition comprises inactive ingredients, such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition, in some embodiments, facilitates administration of the compound to a mammal.

In another embodiment, a pharmaceutical composition comprises a compound of the invention, and/or a pharmaceutically acceptable salt thereof, as an active ingredient in free-acid or free-base form, or in a pharmaceutically acceptable salt form. In another embodiment, the pharmaceutical compositions described herein include the use of N-oxides (if appropriate), crystalline forms, amorphous phases, as well as active metabolites of these compounds having the same type of activity.

In another embodiment, pharmaceutical compositions described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, enteric coated formulations, pulsatile release formulations, multiparticulate formulations, and mixed immediate and controlled release formulations.

In another embodiment, the compound of the invention, or a pharmaceutically acceptable salt thereof, is administered systemically. In another embodiment, the compound of the invention, or a pharmaceutically acceptable salt thereof, is administered orally. All formulations for oral administration are in dosages suitable for such administration. In another embodiment, the solid dosage forms disclosed herein are in the form of a tablet, a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In another embodiment, the pharmaceutical formulation is in the form of a tablet. In another embodiment, the pharmaceutical formulation is in the form of a suspension tablet, a fast-melt tablet, a bite-disintegration tablet, a rapid-disintegration tablet, an effervescent tablet, or a caplet. In another embodiment, pharmaceutical formulation is in the form of a capsule.

In another embodiment, the pharmaceutical solid oral dosage forms are formulated to provide a controlled release of the active compound. Controlled release profiles include, for example, sustained release, prolonged release, pulsatile release, and delayed release profiles.

In another embodiment, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

In another embodiment, for buccal or sublingual administration, the compositions optionally take the form of tablets, lozenges, or gels formulated in a conventional manner.

In another embodiment, a compound of the invention, or a pharmaceutically acceptable salt thereof, is formulated into a pharmaceutical composition suitable for intramuscular, subcutaneous, or intravenous injection. Parenteral injections involve either bolus injection and/or continuous infusion.

In another embodiment, a compound of the invention, or a pharmaceutically acceptable salt thereof, is administered intravenously. In another embodiment, a compound of the invention, or a pharmaceutically acceptable salt thereof, is administered subcutaneously.

In another embodiment, a compound of the invention, or a pharmaceutically acceptable salt thereof, is administered topically. In such embodiments, a compound of the invention, or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. In another embodiment, a compound of the invention, or a pharmaceutically acceptable salt thereof, is administered topically to the skin of mammal. In another embodiment, a compound of the invention is prepared as a transdermal dosage form.

In another embodiment, there is provided use of a compound of the invention, or a pharmaceutically acceptable salt thereof, in the manufacture of a medicament for treating a disease, disorder or conditions. In some embodiments, the treatment of the disease, disorder or conditions requires or involves bacteria eliminated.

The dosage of the inventive compositions or extract may vary depending on, for example, the body weight, age, sex, health condition, diet, time of administration, method of administration, excretion rate and disease severity for a certain patient.

In another embodiment, the composition described herein is prepared as a prodrug. A "prodrug" refers to an agent that is converted into the parent drug in vivo. In another embodiment, the design of a prodrug increases the effective water solubility. An example, without limitation, of a prodrug is a compound, which is administered as an ester (the "prodrug") but then is metabolically hydrolyzed to provide the active entity. In certain embodiments, upon in vivo administration, a prodrug is chemically converted to the biologically, pharmaceutically or therapeutically active form of the composition.

In another embodiment, protected derivatives of the disclosed composition are also contemplated. A variety of suitable for use with the disclosed composition is disclosed in Greene and Wuts Protective Groups in Organic Synthesis; 3rd Ed.; John Wiley & Sons, New York 1999.

In another embodiment, the compounds described herein are labeled isotopically (e.g. with a radioisotope) or by another other means, including, but not limited to, the use of chromophores or fluorescent moieties, bioluminescent labels, or chemiluminescent labels.

In another embodiment, the composition is formulated in a pharmaceutically acceptable composition which refers to a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

In another embodiment, the compositions described herein are formulated into pharmaceutical compositions. Pharmaceutical compositions of the invention are formulated in a conventional manner using one or more pharmaceutically acceptable inactive ingredients that facilitate processing of the active compounds into preparations that are used pharmaceutically.

A formulation depends upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In another embodiment, a pharmaceutical composition comprises a mixture of the peptide of this invention and at least one additional active ingredient. In another embodiment, a pharmaceutical composition comprises inactive ingredients, such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition, in some embodiments, facilitates administration of the compound to a mammal.

In another embodiment, for buccal or sublingual administration, the compositions optionally take the form of tablets, lozenges, or gels formulated in a conventional manner.

In another embodiment, a compound of the invention, or a pharmaceutically acceptable salt thereof, is formulated into a pharmaceutical composition suitable for intramuscular, subcutaneous, or intravenous injection. Parenteral injections involve either bolus injection and/or continuous infusion.

In another embodiment, a compound of the invention, or a pharmaceutically acceptable salt thereof, is administered topically. In such embodiments, a compound of the invention, or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. In another embodiment, a compound of the invention, or a pharmaceutically acceptable salt thereof, is administered topically to the skin of mammal. In another embodiment, a compound of the invention is prepared as a transdermal dosage form.

In one embodiment, the compound of the invention, or a pharmaceutically acceptable salt thereof, is used in the preparation of medicaments for the treatment of diseases or conditions in a mammal which include pathogenic bacteria infection. Methods for treating any of the diseases or conditions described herein in a mammal in need of such treatment, involves administration of pharmaceutical compositions that include the compound of the invention, or a pharmaceutically acceptable salt, N-oxide, active metabolite, prodrug, or pharmaceutically acceptable solvate thereof, in therapeutically effective amounts to the mammal.

Therapeutically effective amounts depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In one embodiment, the methods of treatment comprise single administration of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year. In another embodiment, "compound" is a peptide as described herein. In another embodiment, "compounds" are peptides as described herein.

In certain embodiments, wherein the patient's condition does not improve, upon the doctor's discretion the compound is administered chronically, that is, for an extended period of time.

In certain embodiments, wherein a patient's status does improve, the dose of drug being administered is temporarily reduced or temporarily suspended for a certain length of time (i.e., a "drug holiday").

In another embodiment, doses employed for adult human treatment are typically in the range of 0.01 mg-5000 mg per day. In another embodiment, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day. In one embodiment, the daily dosages appropriate for the compound of the invention, or a pharmaceutically acceptable salt thereof, described herein are from about 0.01 to about 50 mg/kg per body weight.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Methods for Treatment

In another aspect, the present disclosure provides a method for eliminating bacteria or inhibiting growth thereof, comprising contacting the bacteria with the peptide or the composition of this invention, thereby eliminating bacteria or inhibiting growth thereof.

In some embodiments, the method comprises exposing the bacteria to an effective concentration of the composition. In some embodiments, the method is for eliminating bacteria. In some embodiments, the method is for inhibiting bacterial growth.

In some embodiments, the method for treating a subject afflicted with a bacterial infection, comprising administering to the subject an effective amount of the peptide or of the composition of this invention, thereby treating a subject afflicted with a bacterial infection.

In one embodiment, the present invention provides a method for treating a subject afflicted with a bacterial infection, comprising contacting bacteria causing the bacterial infection with the peptide or the composition of this invention.

In another embodiment, the present invention provides a method for preventing, inhibiting or treating a subject afflicted with a bacterial infection e.g., neonatal infection, meningitis, neonatal meningitis, hemorrhage, mastitis, dermatitis, upper respiratory tract infection, bronchitis, necrosis otitis, urinary tract infection, cholecystitis, diarrhea, gastroenteritis, enterocolitis, peritonitis, endocarditis, pneumonia, sepsis, septic shock, septicemia, septic arthritis, thrombophlebitis, hemolytic-uremic syndrome, osteomyelitis, salmonellosis, typhoid fever, and wound infection, comprising contacting the peptide or the composition of this invention with the bacteria selected from, without being limited thereto, *Micrococcus luteus, Staphylococcus aureus, Staphylococcus epidermidis, Staphylococcus hominis, Streptococcus agalactiae, Lactobacillus casei, Klebsiella pneumoniae, Enterococcus faecalis, Escherichia coli, Pseudomonas aeruginosa, Salmonella enterica*, or any combination thereof, thereby treating a subject afflicted with a bacterial infection.

In some embodiments, the present invention provides a method for reducing or eliminating bacteria or inhibiting growth thereof, on a surface, comprising contacting the surface with the peptide or the composition of the invention. In one embodiment, the surface is a surface utilized for food processing or food manufacturing. In one embodiment, the surface is a surface utilized by a subject having a compromised immune system such as but not limited to a new born. In one embodiment, the surface is a surface in a hospital or a surface utilized by a medical professional. In one embodiment, the surface is a surface used for a medical procedure. In one embodiment, the present invention provides a coating for a medical device, wherein the coating comprises the peptide of the invention.

In some embodiments, the medical device is selected from, but not limited to: catheter, stent, fiber, non-woven fabric, vascular graft, dental filling material, materials for approximation, adhesion of tissues, materials used in osteosynthesis (e.g. pin or bone screw), cardiac patch, suture, soft and hard tissue scaffold and filler (e.g. collagen, calcium phosphate, bioglass), bone void filler intended for the repair of bone defect, intrauterine device, root canal filler, drug delivery pump, implantable infusion pump, spacer device, implant containing medicinal product, and scaffold for tissue engineering.

According to some embodiments of the present invention, there is provided a method for eliminating or inhibiting growth of soil bacteria. In some embodiments, the method is for inhibiting overall damage to a plant or plant part. In some embodiments, the composition is applied to the soil using methods known in the art. These include but are not limited to: (a) drip irrigation or chemigation; (b) soil incorporation; (c) seed treatment.

General

As used herein the term "about" refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments unless the embodiment is inoperative without those elements.

Various embodiments and aspects of the present invention as delineated hereinabove and as claimed in the claims section below find experimental support in the following examples.

EXAMPLES

Reference is now made to the following examples which, together with the above descriptions, illustrate the invention in a non-limiting fashion.

Generally, the nomenclature used herein and the laboratory procedures utilized in the present invention include chemical, molecular, biochemical, and cell biology techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); "Cell Biology: A Laboratory Handbook", Volumes I-III Cellis, J. E., ed. (1994); The Organic Chemistry of Biological Pathways by John McMurry and Tadhg Begley (Roberts and Company, 2005); Organic Chemistry of Enzyme-Catalyzed Reactions by Richard Silverman (Academic Press, 2002); Organic Chemistry (6th Edition) by Leroy "Skip" G Wade; Organic Chemistry by T. W. Graham Solomons and, Craig Fryhle.

Example 1

Structural Characterization of Phenol-Soluble Modulin (PSM)-α3 Fragment

This invention discloses novel antimicrobial peptides (AMPs) which are fibril-forming segments of PSMs and determined their micro-crystal structures, presenting the first structures of bacterial amyloids. The structures reveal different amyloid states that were correlated to specific PSMs activities.

FIG. 1A shows that LFKFFK peptide (SEQ ID NO: 1) forms a completely new amyloid fibril assembly of a trimeric arrangement of antiparallel β-sheets that creates elongated cylindrical cavities running along the fibril-like structure. This architecture is fundamentally different from the canonical steric-zipper β-structure of typical amyloid-like segments, but reminiscent of that displayed by a polymorph of Amyloid-β fibrils and prion fragments. Cylindrical and antiparallel arrangements are both linked to toxicity. In addition, the elongated fibril is characterized by a distance of 4.6-4.8 Angstrom between individual β-strands. FIG. 1B illustrates the other form of LFKFFK peptide (SEQ ID NO: 1). This fibril conformation is composed of out-of-register β-sheets, which was found to form toxic amyloid aggregates.

Example 2

Anti-Bacterial Activity

Materials and Methods

The anti-bacterial activity of LFKFFK peptide (SEQ ID NO: 1), KLFKFFK peptide (SEQ ID NO: 3) and control peptides with a hydrophobic/cationic amino-acid composition, IIKVIK (SEQ ID NO: 10) and IIKIIK (SEQ ID NO: 11), was examined by determining the diameter of the growth inhibition of *Micrococcus luteus* cells.

N-terminal acetylation of peptides is known to enhance fibril formation. Therefore, the bacterial growth of *Staphylococcus hominis* was tested by capped peptides of SEQ ID NO: 1 and 2. The determination of the minimal inhibition concentration (MIC), which is the lowest concentration able to visibly inhibit growth of *Staphylococcus hominis*, was determined by measuring the $O.D_{600\ nm}$ after 24 hours incubation at 37° C. with agitation. The lowest concentration at which no growth was observed is determined as the MIC. The experiment was performed in triplicates.

Extended fragments of the LFKFFK (SEQ ID NO: 1) sequence were derived from *Staphylococcus aureus* (PSMα3 derivatives) in order to determine the minimum peptide length critical for the antibacterial activity. A 22-residue peptide with the sequence: MEFVAKLFKFFKDLLG-KFLGNN (SEQ ID NO: 2) is known to lack an antibacterial activity. Therefore, the antibacterial activity of its fragments comprising SEQ ID NO: 1, as listed in Table 1, were examined on the growth of *Staphylococcus epidermidis* ATCC 12228 cells, *Staphylococcus hominis*, and *Lactobacillus casei* after 24 hours from treatment with 0.5 mM peptide at 37° C. under agitation compared to control (bacterial growth w/o peptide). *Lactobacillus casei* are probiotic bacteria. Therefore, the peptides listed in Table 1 were also tested against bacteria of the human flora.

TABLE 1

| SEQ ID NO: | Sequence |
| --- | --- |
| 1 | Ac-LFKFFK-NH$_2$ |
| 3 | Ac-KLFKFFK-NH$_2$ |
| 4 | Ac-KLFKFFKD-NH$_2$ |
| 5 | Ac-KLFKFFKDL-NH$_2$ |
| 6 | Ac-KLFKFFKDLL-NH$_2$ |
| 7 | Ac-KLFKFFKDLLG-NH$_2$ |
| 8 | Ac-AKLFKFFKDLLGK-NH$_2$ |
| 9 | Ac-VAKLFKFFKDLLGKFL-NH$_2$ |

Results

FIGS. 2A-B indicate that LFKFFK (SEQ ID NO: 1) and KLFKFFK (SEQ ID NO: 3) peptides have anti-bacterial activity. FIG. 2A illustrates that these peptides, but not control peptides, inhibit the growth of *Micrococcus luteus*. The crystal structure of these two control peptides revealed a different amyloid-like form, of the canonical steric-zipper β-structure of amyloid-like segments (not shown). In addition, FIG. 2B shows a dose-dependent effect of the peptides: LFKFFK (SEQ ID NO: 1) and KLFKFFK (SEQ ID NO: 3), and that KLFKFFK peptide (SEQ ID NO: 3), is even more toxic to *Micrococcus Luteus*.

Figure 4:
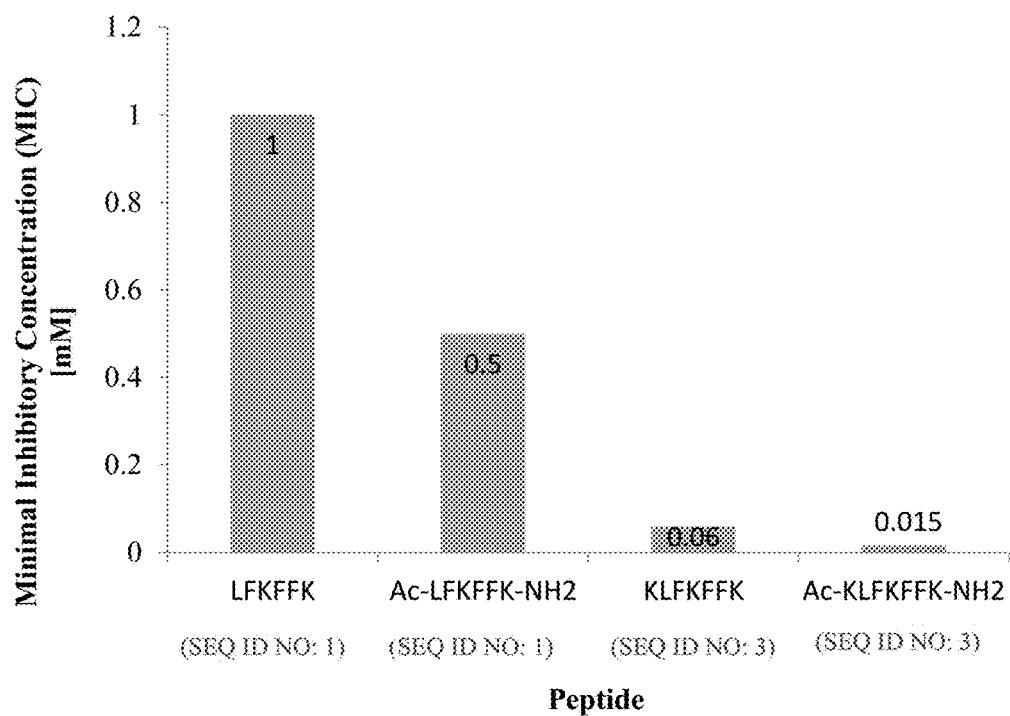
FIG. 4 presents a bar graph demonstrating the minimal inhibition concentration (MIC) of LFKFFK (SEQ ID NO: 1), KLFKFFK (SEQ ID NO: 3), and their capped forms against *Staphylococcus hominis*.

FIG. 3 illustrate the growth inhibition of *Staphylococcus hominis* after treatment with various concentrations of the acetylated peptides, while the most potent peptide against *Staphylococcus hominis* is Ac-KLFKFFK-NH$_2$ (SEQ ID NO: 3) with a MIC of 15 as shown in FIG. 4.

Figure 5:
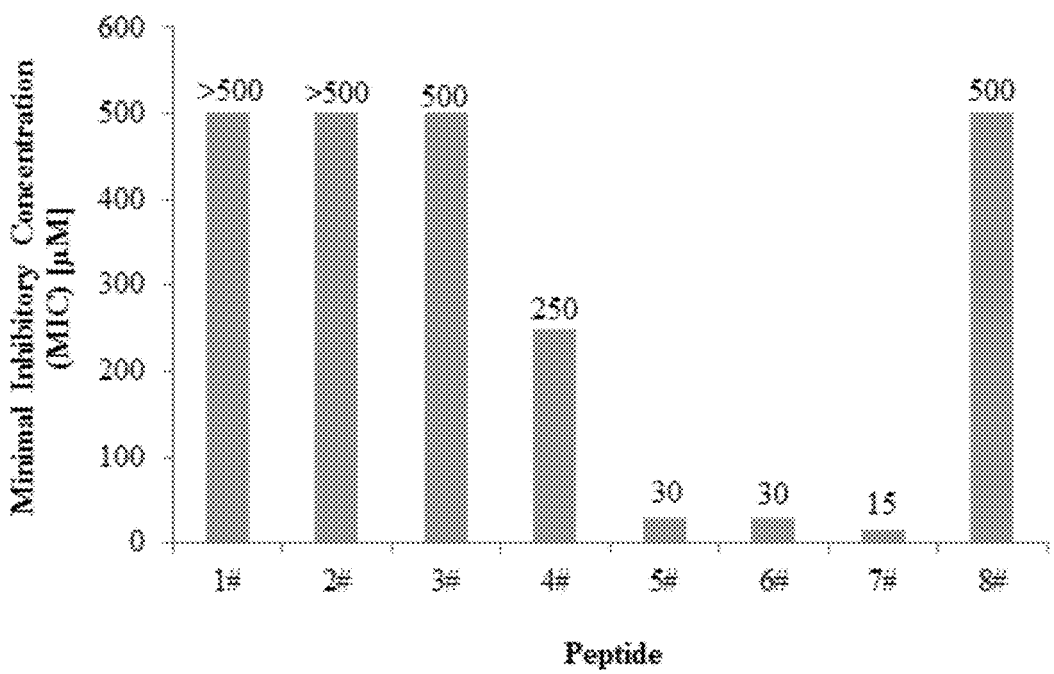
FIG. 5 presents a bar graph demonstrating the MIC of several fragments comprising SEQ ID NO: 1, as listed in Table 1, against *Staphylococcus epidermidis* ATCC 12228.

Extended fragments of the LFKFFK sequence (SEQ ID NO: 1) including peptides 5 (Ac-KLFKFFKDLL-NH$_2$; SEQ ID NO: 6) and 6 (Ac-KLFKFFKDLLG-NH$_2$; SEQ ID NO: 7) show better anti-bacterial activity, as shown in FIG. 5. However, peptide 8 fails to exhibit any antibacterial activity.

Figure 6:
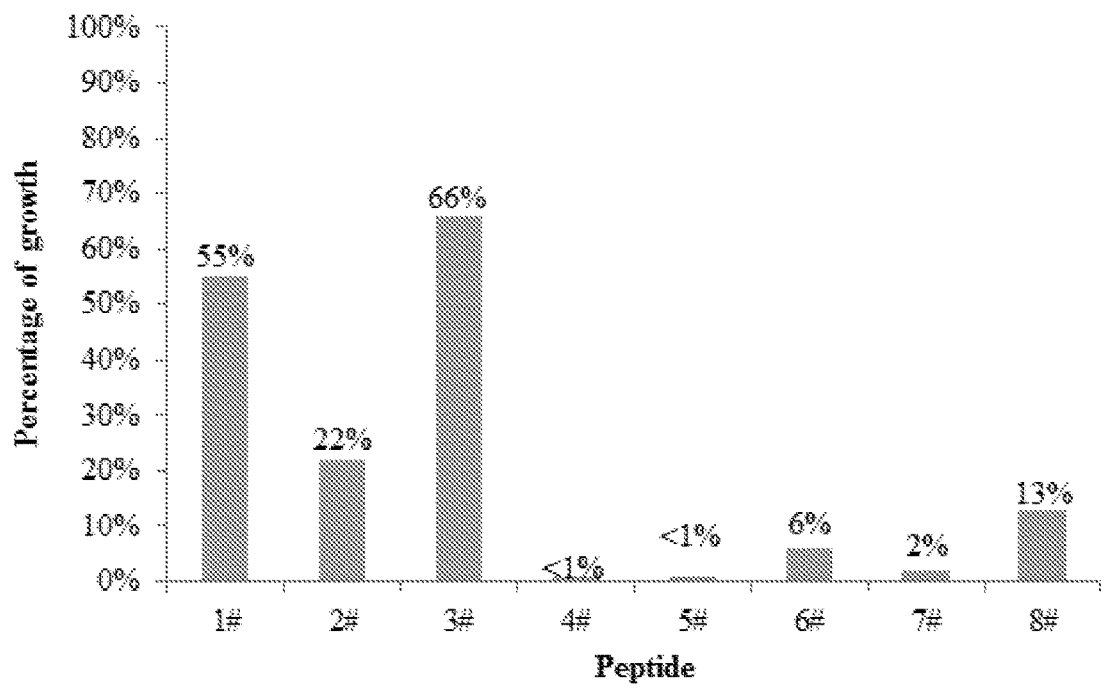
FIG. 6 presents a bar graph demonstrating the growth of *Staphylococcus hominis* after treatment with 0.5 mM of fragments comprising SEQ ID NO: 1, as listed in Table 1, compared to control (w/o peptide).

FIG. 6 demonstrates that the short peptides 1-3 (SEQ ID NO: 1, 3, and 4) are partially active against *S. hominis*, whereas the enlarged peptides 4-8 (SEQ ID NO: 5-9) exhibited a beneficial antibacterial effect. Thus, the length of the peptide is not predictive of its antibacterial activity.

Figure 7:
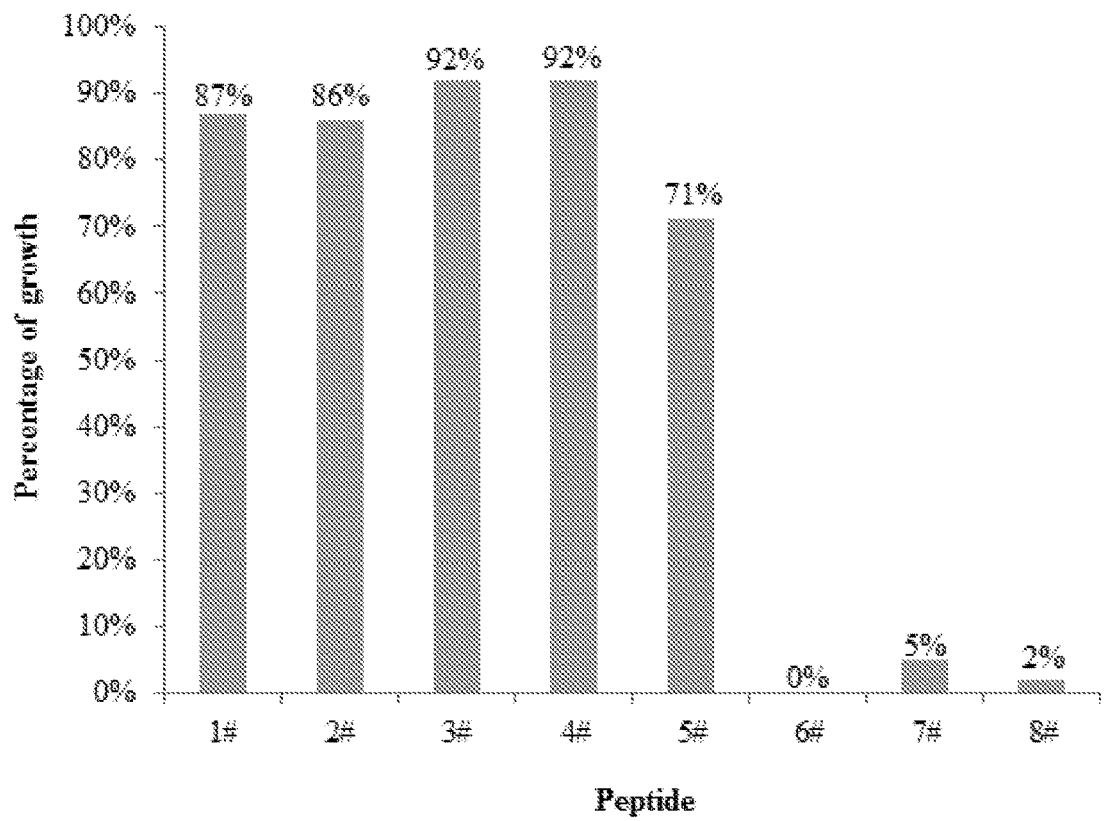
FIG. 7 presents a bar graph demonstrating the growth of *Lactobacillus casei* after treatment with 0.5 mM of fragments comprising SEQ ID NO: 1, as listed in Table 1, compared to control (w/o peptide).

FIG. 7 demonstrates that peptides 6-8 (SEQ ID NO: 7-9) exhibited an antibacterial effect against *L. casei* whereas the shorter peptides were inactive. These results suggest species-specific antibacterial activity that could protect the human flora.

In summary, the results indicate that the antibacterial activity of the various derivatives is bacterium-specific.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A peptide comprising SEQ ID NO: 1 (LFKFFK), wherein said peptide comprises up to 20 amino acid residues, and wherein N-terminus of said peptide is acetylated or C-terminus of said peptide is amidated.

2. The peptide of claim 1, wherein the peptide is up to 16 amino acid residues long.

3. The peptide of claim 1, wherein the peptide is up to 11 amino acid residues long.

4. The peptide of claim 1, the peptide comprising the amino acid sequence selected from the group consisting of: SEQ ID NO: 1 (LFKFFK), SEQ ID NO: 3 (KLFKFFK), SEQ ID NO: 4 (KLFKFFKD), SEQ ID NO: 5 (KLFKFFKDL), SEQ ID NO: 6 (KLFKFFKDLL), SEQ ID NO: 7 (KLFKFFKDLLG), SEQ ID NO: 8 (AKLFKFFKDLLGK), and SEQ ID NO: 9 (VAKLFKFFKDLLGKFL).

5. The peptide of claim 1, wherein the N-terminus acetylated or the C-terminus amidated peptide consists of the amino acid sequence selected from the group consisting of: SEQ ID NO: 1 (LFKFFK), SEQ ID NO: 3 (KLFKFFK), SEQ ID NO: 4 (KLFKFFKD), SEQ ID NO: 5 (KLFKFFKDL), SEQ ID NO: 6 (KLFKFFKDLL), SEQ ID NO: 7 (KLFKFFKDLLG), SEQ ID NO: 8 (AKLFKFFKDLLGK), and SEQ ID NO: 9 (VAKLFKFFKDLLGKFL).

6. The peptide of claim 1, wherein the N-terminus of said peptide is acetylated.

7. The peptide of claim 1, wherein the peptide is in the form of a β-strand.

8. The peptide of claim 1, wherein said peptide is characterized by antimicrobial activity.

9. The peptide of claim 1, wherein said peptide is characterized by a minimal inhibition concentration (MIC) of less than 500 μM.

10. A composition comprising at least one peptide of claim 1 and a carrier.

11. The composition of claim 10, comprising at least three different peptides, wherein said peptides are in the form of antiparallel β-strand.

12. The composition of claim 10, wherein said composition is a pharmaceutical composition.

13. A method for eliminating bacteria or inhibiting growth thereof, the method comprising contacting said bacteria with a peptide comprising SEQ ID NO: 1 (LFKFFK), wherein said peptide comprises up to 20 amino acid residues, thereby eliminating bacteria or inhibiting growth thereof.

14. The method of claim 13, wherein said eliminating bacteria or inhibiting growth thereof comprises eliminating bacteria or inhibiting growth thereof on a surface.

15. The method of claim 13, wherein said eliminating bacteria or inhibiting growth thereof is in a subject afflicted with a bacterial infection.

16. The method of claim 13, wherein said bacteria is: Gram-positive bacteria, Gram-negative bacteria, or both.

17. The method of claim 13, wherein said bacteria is selected from the group consisting of: *Staphylococcus aureus, Staphylococcus epidermidis, Staphylococcus hominis, Streptococcus agalactiae, Lactobacillus casei, Klebsiella pneumoniae, Entrococcus faecalis, Escherichia coli, Pseudomonas aeruginosa, Salmonella enterica*, and any combination thereof.

18. The method of claim 15, wherein said peptide is in an amount sufficient to eliminate bacteria but refractory to a eukaryotic cell.

19. The method of claim 15, wherein said contacting comprises administering to said subject an effective amount of said peptide, thereby treating bacterial infection in said subject.

* * * * *

SEQUENCE LISTING

```
<160> NUMBER OF SEQ ID NOS: 9

<210> SEQ ID NO 1
<211> LENGTH: 6
<212> TYPE: PRT
<213> ORGANISM: Staphylococcus aureus

<400> SEQUENCE: 1

Leu Phe Lys Phe Phe Lys
1               5

<210> SEQ ID NO 2
<211> LENGTH: 22
<212> TYPE: PRT
<213> ORGANISM: Staphylococcus aureus

<400> SEQUENCE: 2

Met Glu Phe Val Ala Lys Leu Phe Lys Phe Phe Lys Asp Leu Leu Gly
1               5                   10                  15
```

Lys Phe Leu Gly Asn Asn
            20

<210> SEQ ID NO 3
<211> LENGTH: 7
<212> TYPE: PRT
<213> ORGANISM: Staphylococcus aureus

<400> SEQUENCE: 3

Lys Leu Phe Lys Phe Phe Lys
1               5

<210> SEQ ID NO 4
<211> LENGTH: 8
<212> TYPE: PRT
<213> ORGANISM: Staphylococcus aureus

<400> SEQUENCE: 4

Lys Leu Phe Lys Phe Phe Lys Asp
1               5

<210> SEQ ID NO 5
<211> LENGTH: 9
<212> TYPE: PRT
<213> ORGANISM: Staphylococcus aureus

<400> SEQUENCE: 5

Lys Leu Phe Lys Phe Phe Lys Asp Leu
1               5

<210> SEQ ID NO 6
<211> LENGTH: 10
<212> TYPE: PRT
<213> ORGANISM: Staphylococcus aureus

<400> SEQUENCE: 6

Lys Leu Phe Lys Phe Phe Lys Asp Leu Leu
1               5                   10

<210> SEQ ID NO 7
<211> LENGTH: 11
<212> TYPE: PRT
<213> ORGANISM: Staphylococcus aureus

<400> SEQUENCE: 7

Lys Leu Phe Lys Phe Phe Lys Asp Leu Leu Gly
1               5                   10

<210> SEQ ID NO 8
<211> LENGTH: 13
<212> TYPE: PRT
<213> ORGANISM: Staphylococcus aureus

<400> SEQUENCE: 8

Ala Lys Leu Phe Lys Phe Phe Lys Asp Leu Leu Gly Lys
1               5                   10

<210> SEQ ID NO 9
<211> LENGTH: 16
<212> TYPE: PRT
<213> ORGANISM: Staphylococcus aureus

```
<400> SEQUENCE: 9

Val Ala Lys Leu Phe Lys Phe Phe Lys Asp Leu Leu Gly Lys Phe Leu
1               5                   10                  15
```